| United States Patent [19] | [11] Patent Number: 4,977,081 |
| --- | --- |
| Raybould et al. | [45] Date of Patent: Dec. 11, 1990 |

[54] STABLE RABBIT-MOUSE HYBRIDOMAS AND SECRETION PRODUCTS THEREOF

[75] Inventors: Torquil J. G. Raybould, North Vancouver; Miyoko Takahashi, Downsview, both of Canada

[73] Assignee: Adi Diagnostics, Inc., Rexdale, Canada

[21] Appl. No.: 504,689

[22] Filed: Apr. 4, 1990

Related U.S. Application Data

[63] Continuation of Ser. No. 189,754, May 3, 1988, abandoned, which is a continuation-in-part of Ser. No. 46,439, May 4, 1987, abandoned.

[51] Int. Cl.$^5$ .......................... C12P 12/00; C12N 5/00; C12N 15/00; G01N 33/53
[52] U.S. Cl. ............................ 435/70.21; 435/240.27; 435/172.2; 935/95; 935/96; 935/102; 935/104; 530/387; 436/548
[58] Field of Search ................... 435/68, 172.2, 240.27; 530/387; 436/548; 935/95, 96, 102, 104

[56] References Cited

PUBLICATIONS

Braun et al., Pathog. Streptococci, Proc. Int. Symp., 7th Meeting, Date 1978, pp. 84–85, Editors: Parker, N. J., Chertsey, Engl.
Kuo et al., Mol. Immunol., vol. 22, pp. 351–359, 1985.
Dreher et al., J. Immunol., vol. 130, pp. 442–448, 1985.
Bruno, G. A., New Techniques in Tumor Localization & Radioimmunoassay, pp. 9–15, 1974, John Wiley & Sons, Editors: Croll, Brady, Hindu & Wallner.
Parker, R. C., In Methods of Tissue Culture, Harper & Roe, Publishers, 1966, p. 193.
Reading, Journ. of Immunol. Methods, 53, 261 (1982).

*Primary Examiner*—Christine Nucker
*Assistant Examiner*—Karen I. Krupen
*Attorney, Agent, or Firm*—Wyatt, Gerber, Burke & Badie

[57] ABSTRACT

Rabbit-mouse hybridomas are cultured immediately after fusion in a suspension medium supplemented with normal rabbit serum. This results in stable hybridomas and provides a source of intact rabbit monoclonal antibody immunoglobulin of defined specificity. A hybridoma which secretes intact rabbit antibody specific for Group A Streptococcus is exemplified. Diagnostic compositions and test kits containing rabbit monoclonal antibodies produced from such hybridomas are described.

18 Claims, No Drawings

STABLE RABBIT-MOUSE HYBRIDOMAS AND SECRETION PRODUCTS THEREOF

This application is a continuation of application Ser. No. 07/189,754, filed May 3, 1988, which in turn is a continuation-in-part of application Ser. No.: 046,439, filed May 4, 1987, now abandoned.

FIELD OF THE INVENTION

This invention relates to the production of rabbit-mouse hybridomas and rabbit monoclonal antibodies. It relates also to compositions and test kits containing diagnostically effective amounts of said antibodies.

BACKGROUND OF THE INVENTION

Hybridoma technology has now reached a level where production of murine monoclonal antibodies is possible against most antigens. Some immunogens however, stimulate poor antibody responses in mice and consequently murine monoclonal antibodies with certain epitope specificities cannot be obtained. Further, murine monoclonal antibodies often have low affinity constants and may therefore be unsuitable for use in diagnostic or immunopurification systems.

Rabbits, on the other hand, produce high titers of high affinity polyclonal antibody when hyperimmunized with most immunogens. The ability to produce rabbit monoclonal antibodies could therefore overcome many of the disadvantages of murine systems. Unfortunately, myelomas are unknown in rabbits, and transformation of rabbit lymphocytes, particularly viral transformation of rabbit B-cells in vitro, has proven difficult.

REFERENCE TO THE PRIOR ART

Without rabbit myelomas to work with, researchers interested in producing rabbit monoclonal antibody have focussed exclusively on interspecies hybridomas i.e., rabbit-mouse hybridomas, as a possible source of rabbit monoclonal antibody. The results have not been encouraging. It is apparent from the relevant published reports that the ability to produce rabbit-mouse hybridomas which secrete intact rabbit monoclonal antibody i.e., an immunoglubulin having both heavy and light chains of rabbit origin, having the intended specificity requires improvement for the technology to be a viable alternative in monoclonal antibody production. Moreover, improved stability of these hybridomas is required to ensure a constant source of the monoclonal antibody.

For example, Yarmush et al. (Proc. Natl. Acad. Sci. U.S.A. 77, 2899 (1980)) describe fusion of spleen cells from a rabbit hyperimmunized with Streptococcus Group C vaccine and a variety of different murine myeloma lines. From an estimated $5-16 \times 10^3$ hybridomas resulting from the fusion, only one hybridoma secreted an intact rabbit monoclonal antibody having specificity for a Streptococcus Group C epitope Attempts to maintain this hybridoma were unsuccessful. Other fusion products either contained no rabbit chromosomes and therefore were incapable of producing rabbit antibody, or produced hybrid antibody, or rabbit antibodies with only heavy or light rabbit chains or could not be maintained long enough to make a determination.

In a later but related report, Kuo et al. (Mol. Immunol 22, 351 (1985) describe production of a rabbit-mouse hybridoma which secretes intact rabbit monoclonal antibody specific for a Group C Streptococcus epitope. Again, however, recovery of a desired clone proved to be a rare event. Moreover, extreme instability of the clone which secreted intact rabbit antibody of known specificity prevented it from being maintained for a sufficient time period.

Those skilled in the art well understand the need for a method by which greater numbers of stable rabbit-mouse hybridomas can be generated by fusion. Unless a large population of stable fusion products is made available, the likelihood that desired hybridomas can be recovered, given chromosomal translocation, rearrangement and shedding which occur upon fusion, is minimal It is therefore an object of the present invention to. provide stable rabbit-mouse hybridomas which secrete rabbit antibody of defined specificity against rabbit antigens.

It is a further object of the present invention to provide a method for producing the stable hybridomas in relative abundance.

It is also an object of the present invention to provide monoclonal rabbit antibody of defined specificity useful in immunopurification or immunodiagnosis.

It is a still further object of this invention to provide diagnostic test kits employing rabbit monoclonal antibody.

SUMMARY OF THE INVENTION

In arriving at the method of the present invention, it was assumed that the inability to obtain stable rabbit-mouse hybridomas which secrete intact rabbit antibody using fusion techniques otherwise satisfactory in producing mouse-mouse hybridomas, may be due to methodology specifically at the post-fusion cloning and stabilization stages of the processes.

Typically, but with occasional variation, mouse-mouse hybridomas are cultured immediately after fusion in a nutrient medium supplemented with fetal calf serum. Horse serum has also been used to supplement the growth medium, but fetal calf serum is most often the growth medium supplement of choice, in practice. Use of this culturing medium has carried over into methods designed to produce interspecies hybridomas such as murine-bovine hybridomas, murine-porcine hybridomas and, as exemplified by the prior art noted above, into methods used to produce rabbit-mouse hybridomas.

By contrast, the method of the present invention avoids the use of fetal calf serum in the culture medium at crucial stages in rabbit-mouse hybridoma methodology i.e., at the stages at which the fusion products are cultured initially for screening and then cloned until stable. Surprisingly, it has been found found that the presence of rabbit serum, rather than fetal calf serum or horse serum, in the. culture medium, results in a greater population of rabbit-antibody secreting rabbit-mouse hybridomas that can be recovered and stabilized. Indeed, when the method of the present invention is practiced, the resulting hybridomas can be present in such abundance that it may be necessary to select a segment of the hybridoma population for subsequent cloning to reduce the procedure to a manageable scale.

Thus, in one of its aspects, the present invention provides a method for stabilizing rabbit-mouse hybridomas which comprises culturing the fusion product of a murine myeloma cell and a rabbit immunocyte in the presence of rabbit serum.

For best results, the presence of the rabbit serum is maintained in the hybridoma culture medium throughout the post-fusion stages encountered in standard hybridoma methodology i.e., during the selection phase, the screening phase and the cloning and the later passive phase of stabilization.

The stable rabbit-mouse hybridomas resulting from the method of the present invention which secrete intact rabbit antibody of defined specificity constitute another aspect of the present invention. Using the methodology of the present invention, a greater proportion of stable rabbit-mouse hybridomas having this desired characteristic can be recovered than has yet been possible. The term defined "specificity" is used herein to describe an antibody with specificity to an epitope on an antigen or hapten with which the rabbit's immunocytes were immunized.

In another of its aspects, the present invention comprises novel rabbit monoclonal antibody of defined specificity such as rabbit monoclonal antibody specific for Group A Streptococcus. Hybridomas referred to herein as "stable" are those rabbit-mouse hybridomas which will survive at least two, preferably three or more cycles of cloning, will grow for at least three months after cloning, can be revived successfully from storage in liquid nitrogen and will secrete rabbit monoclonal antibody in detectable amounts when cultured appropriately.

DESCRIPTION OF THE PREFERRED EMBODIMENTS

Apart from the use of rabbit serum rather than fetal calf serum or horse serum, the method of the present invention is not unlike the techniques in current use for preparing murine-murine hybridomas. The difference in result can be staggering, however. For the most part, those skilled in the art will readily understand what is required to implement the method of this invention. Reference may be made to the text "Hybridoma Technology in the Biosciences and Medicine", Plenum Press, New York, 1985 and, to the text "Practical Immunoassay—The state of the Art: Marcel Dekker Inc., New York, 1984, pp. 199-215 and to the prior publications noted previously herein. Accordingly, no effort is made herein to elaborate on the numerous possible variations to the initial and subsequent stages common to known procedures. These variations have been given consideration in the literature.

Rabbit serum used in the method of the present invention can be extracted, in a conventional manner, such as by separation from the blood of rabbits. From our observations, it is apparent that serum from some rabbits is better able to support growth of the hybridomas and it is therefore recommended that one screen serum collected from individual rabbits by determining first whether each serum will support growth of murine myeloma cells intended to be used in the fusion process. An indication of growth in particular serum within about one week after culturing is a strong indication that the serum is suitable for use in the method described herein.

Individual sera which support murine mylemoma growth may then be pooled, if desired, to provide stock serum for supplementing mammalian cell growth medium. It should be appreciated that the initial serum screening step is not absolutely essential to the success of the present method. It does, however, provide for improved results and does assist in ensuring that the myeloma line and therefore the resulting rabbit-mouse hybridoma are able to adapt to growth in the presence of rabbit serum.

As a further measure, it is preferred herein to heat inactivate the serum before it is used in the process. This practice is common to horse serum production and is therefore known to those skilled in this art. Exposure of the serum for about 30 minutes to a temperature around 56° C. is adequate to ensure inactivation, although variations to this regimen may be suitable.

The rabbit serum will be present with the antibody-secreting hybridomas during critical stages in the process, including screening of the supernatant for antibody activity and it is therefore important that the serum is not extracted from a rabbit immunized with the immunogen, by prior exposure, against which monoclonal antibody is to be raised. Clearly, wells containing such rabbit serum will always test positive for the presence of that particular antibody. Preferably, the rabbit serum used herein will not be extracted from a rabbit hyperimmunized with immunogen of any nature although serum of a rabbit hyperimmunized to produce antibody immunologically distinct from the desired monoclonal antibody may be used, if necessary. It is most preferred to use serum extracted from young, healthy rabbits which have not been hyperimmunized i.e., from normal rabbits. Consequently, we refer herein to the rabbit serum of preference as normal rabbit serum.

Selection of cells appropriate for fusion in the method of this invention is as important to success as is the case in mouse-mouse hybridoma methodology or any other hybridoma technology. Known murine myelomas lines may be used provided that they satisfy the established criteria of:

1. ability to grow well in vitro,
2. to fuse well with antibody-secreting rabbit immunocytes,
3. to produce stable rabbit-mouse hybridomas,
4. to express a selectable phenotype and,
5. ideally, not to produce or secrete antibody.

In addition, and as mentioned above, the murine myeloma line selected for use should have demonstrated the capacity to adapt to growth in the presence of rabbit serum.

Many suitable murine myeloma lines are available: P3/X63-Ag 8 (ATCC TIB9) and 45.6TG1.7 (ATCC CRL 1608) which synthesize and secrete intact murine immunoglobulin; and P3/NS/1-Ag4-1 (ATCC TIB8) and P3x63 Ag8U.1 (ATCC CRL 1597) which produce but do not secrete L chains. Because it does not produce murine immunoglobulin and is amenable to growth in the presence of normal rabbit serum, the murine myeloma cell line designated Sp 2/0-Ag14 (ATCC CRL 1581) is preferred for use herein although any line which possesses the same desirable characteristics as Sp 2/0-Ag14 may be used such as FO (ATCC CRL 1646). Each line is available from the American Type Culture Collection in Rockville, Md., U.S.A. where it is further identified by the accession number quoted in parentheses above.

Immunocytes useful herein are extracted from hyperimmunized rabbits e.g. may be obtained from the spleen, lymph nodes or peripheral circulation of the hyperimmunized rabbit. Hyperimmunization is accomplished using well established protocol. Titer of antibody in the serum of the rabbit is monitored during the course of the immunization schedule in the usual manner until an acceptable titre is detected and then a booster injection of immunogen is administered about 1 to 3 days prior to immunocyte extraction. We prefer to extract immunocytes from the spleen simply because it offers a larger, concentrated population of immunocytes than do the other potential sources.

The preferred process by which murine myelomas and rabbit immunocytes are fused is very similar to conventional fusion protocols. Parent cells are suspended in standard mammalian cell growth medium after washing to remove residual serum and counted. A predetermined ratio of immunocytes: myelomas, for example 1:1 to 20:1, preferably 5:1 to 10:1 and ideally around 5:1, is co-pelleted and then presented with fusant, preferably polyethylene glycol. There are many different grades of polyethylene glycol which are commercially available particularly for this purpose. We prefer to use PEG4000 (a product of Merck & Co., Inc. Rahway, N.J., U.S.A.). The concentration of polyethylene glycol in the fusion suspension may vary but, given the success achieved to date, we presently prefer a concentration of about 43% w/v of fusion suspension.

Fusion is initiated by addition of the polyethylene glycol and reaction continued at about 37° C. Fusion products are then pelleted, additional aliquots of mammalian cell growth medium are added at intervals, then the suspension is centrifuged to concentrate the fusion products and the supernatant is aspirated; all of these steps being in accordance with protocol previously established in the art particularly as regards timing.

The mammalian cell growth medium in which parent lines are cultured, in which fusion is carried out and in which the fusion products are cultured can be any medium having a nutrient constitution adequate for maintaining mammalian cells. Media which have been formulated for use specifically in hybridoma production are commercially available. For example, RPMI (a product of Gibco Laboratories, Grand Island, N.Y.) which is used routinely in mouse-mouse hybridoma production is suitable for use herein. We prefer Dubelcco's modified Eagle's medium (a product of Gibco), although, provided the selected medium is appropriately buffered and supplemented with essential metabolites such as sodium pyruvate and glutamine and preferably also contains antimicrobial agents such as penicillin and/or streptomycin, either medium may be used.

It is to this growth medium that other supplements are added to prepare culture medium suitable for culturing fusion products at the various stages in the methodology proposed herein. The growth medium may be used per se to culture rabbit immunocytes, and to culture mouse myelomas although, in the latter case, it is preferably supplemented with normal rabbit serum to confirm the ability of the myelomas to adapt to the presence of the serum. The growth medium is preferably also used per se to conduct the actual fusion. It is however, important that the fusion products are cultured in the presence of growth medium supplemented with rabbit serum, at least until the fusion products are stable. The growth medium may be supplemented with an amount of rabbit serum, e.g. normal rabbit serum which has been heat inactivated, in the range from about 5% to about 25% serum by volume based on the volume of growth medium, more preferably in the range from 10-20% and ideally, according to present experience, around 15%. Higher proportions may not be economically feasible and may even be deleterious without consequent modification—lower proportions are unlikely to provide the desired effect conferred by the rabbit serum. It should be appreciated, however, that these ranges are offered merely as a guideline to provide enhanced fusion results and should not be considered to be definitive in all circumstances. For convenience here, growth medium supplemented with rabbit serum is referred to as rabbit-mouse hybridoma (RMH) culture medium.

Thus, after subjecting the co-pelleted parent cells to the fusion influence of polyethylene glycol, the fusion products are, in accordance with the present invention, resuspended in RMH culture medium. According to standard protocol, residual myelomas and interfusions thereof are preferably selected against in this stage of the process. Thus, the RMH culture medium in which the fusion products are suspended after fusion is one which has been supplemented with a selection agent which prevents unfused cells from surviving in culture, such as HAT in the case where the murine myelomas are susceptible thereto.

In accordance with an embodiment of the invention which is preferred, fusion products are incubated in the RMH culture medium supplemented with selection agent under $CO_2$ atmosphere and then transferred to wells for further analysis and screening. Addition of feeder cells to the wells is preferred in accordance with standard practice. However, whereas it is more common to use splenocytes/thymocytes, we have found that better results are obtained when a feeder layer of murine peritoneal exudate cells, obtained from the peritoneum of healthy mice, is used.

The medium in those wells in which growth is observed is then assayed for the presence of antibody i.e., antibody against immunogen with which the rabbit was hyperimmunized, using, for example, an ELISA assay. The suspensions which elicit a positive result are then typically transferred after appropriate dilution in RMH culture medium to separate wells, observed for growth, re-assayed for antibody secretion and then cloned in the presence of RMH culture medium as many times as are required to be confident of their stability e.g., at least two, preferably three or more cloning cycles.

Those skilled in this art will appreciate that much of the methodology described above is routine. However, minor modifications, particularly to the culture medium by supplementation with normal rabbit serum rather than fetal calf serum or horse serum, do result in much improved yield of rabbit-mouse hybridomas which secrete intact rabbit antibody of defined spedificity e.g., having the expected and desired specificity.

In the examples which follow, we describe a procedure designed to generate rabbit-mouse hybridomas which secrete intact rabbit monoclonal antibody specific for Group A Streptococcus carbohydrate. It will be noted that when the hybridomas are cultured in the presence of fetal calf serum, no hybridomas were successfully cloned. Culturing in the presence of normal rabbit serum resulted not only in a greater number of primary hybridomas but also in a greater proportion of stable, specific-antibody-secreting clones (95%).

An exemplary hybridoma, identified herein as RMH-B52 has been deposited with the American Type Culture Collection, 12301 Parklawn Drive, Rockville, Md. 20852-1776 under accession number HB9696 deposited Apr. 26, 1986. It will be made available to those entitled access to it during pendency of this application and, upon issue of a patent herefor, will be available from the depository without restriction, to those requesting access. This particular cell line is able to secrete rabbit antibody specific for a Group A Streptococcus carbohydrate epitope. It may be cultured in media as exemplified herein.

It is recognized that because rabbit serum is present in the medium in which hybridomas secreting rabbit antibody are cultured, components in the serum may complicate rabbit antibody extraction and purification. It is recommended therefore that, prior to antibody production on a commercial scale for use for example in immunodiagnosis, the hybridomas be adapted gradually to grow in the presence of a non-rabbit serum i.g. fetal calf serum. Background contamination in antibody extractant can be reduced in this way. It is clear from current observations that hybridomas stabilized and cloned in the presence of normal rabbit serum adapt well to the serum adjustment from rabbit serum to fetal calf serum when the adjustment is permitted gradually.

Although, by way of illustration, this invention will be exemplified principally with reference to Group A Streptococci, it will be apparent that the process of the invention is applicable to any rabbit immunogens, i.e., any molecule which stimulates the formation of a rabbit antibody. With all such immunogens stable rabbit-mouse hybridomas can be produced in accordance with the invention and useful monoclonal antibodies can be obtained. Since rabbits respond immunogenically to virtually every infection with which man is afflicted, the value of the invention for providing diagnostic tools to test for human infections particularly bacterial and viral infections is clear.

Suitable rabbit monoclonal antibodies can be produced to test for sexually transmitted diseases such as syphilis caused by *Treponoma pallidum,* gonorrhea from a *Neisseria gonorrhoeae* infection, and Chlamydiae infections which are a major cause of blindness in third world countries. The monoclonal antibodies of this invention can be used to test for pneumococci infections, and for various viral infections such as herpes infections, mononucleosis or hepatitis, as well as protozoal infections such as Rocky Mountain Spotted Fever.

Any of a large number of clinical tests where monoclonal and polyclonal antibodies have been previously used may be employed utilizing the rabbit antibodies derived from the stable hybridomas of this invention. These tests will typically involve the formation of a detectable reaction product between the rabbit antibody and the antigen the presence of which the test is designed to detect. These tests usually take one of two forms. In one class of test the rabbit antibody will be labelled. In another a labelled antibody forms a complex with the antigen and this complex then reacts with the rabbit antibody to form a detectable complex comprising labelled antibody/antigen/rabbit antibody.

Typical tests include radioimmunoassay, enzyme linked immunoassay, precipitation, agglutination, direct and indirect immunofluorescence and complement fixation.

Useful labels include fluorescent labels such as fluorescein, rhodamine, auromine or phycoerythrin. Radioisotopes such as $^{14}C$, $^{131}I$, $^{125}I$ and $^{35}S$ may be employed. Enzyme labels which may be utilized include, for example, β-glucamidase, β-D-glucosidase, β-D-glactosidase, glucose-6-phosphate dehydrogenase, maleate dehydrogenase, urease and glucose oxidase plus peroxidase. Methods of labelling biological products such as cells, antibodies, antigens and antisera are well known and need not be described here.

There are several currently available procedures for detecting these labels including, for example colorimetric, spectrophotometric, fluorospectrophotometric, photometric and gasometric techniques, as well as various instrumental methods of detecting isotopes.

The term "detect" as used herein includes either or both of qualitative recognition that the rabbit antibody is present in a reaction product, and quantitative determination of the amount of reaction product or rabbit antibody present.

The antibodies of the present invention may be adopted for utilization in the enzyme-linked immunosorbent assay (ELISA), and the homogeneous enzyme immunoassay, also known as enzyme multiplied immunoassay (EMIT). Both of these testing methods are well known in the art.

The antibodies may also be employed in "2-site" or "sandwich" assays In a typical assay of this nature, a quantity of antibody is bound to a solid support that is insoluble in the fluid being tested and a quantity of soluble antibody bearing a label that permits detection of the ternary complex formed between the labeled antibody, the antigen and the solid phase antibody is added. As applied to this invention, the rabbit antibody will usually be the labelled antibody, but the rabbit antibody may also be the solid phase antibody.

The solid support surface used in the various tests may be chosen from any of a wide variety of materials such as latex, glass, silica, nylon, polyethylene, polystyrene, polyvinyl chloride and polycarbonate.

All of the tests which may be usefully employed in accordance with this invention involve the formation of a detectable reaction product which includes a monoclonal rabbit antibody derived from a stable rabbit-mouse hybridoma of the invention and an antigen containing an epitope to the antibody.

In one test which is applicable when suitable instrumentation is available, blood from the individual under test is incubated at about 20° to 45° C. in a buffer such as phosphate buffered saline at pH 7.2 to 7.6 with a mixture containing a monoclonal antibody of the invention in labeled form. If there is a positive reaction, the reaction product of the antigen labelled antibody can be detected using an instrument adapted to the selected label.

A kit for this test would contain buffer and a diagnostic amount of a labeled monoclonal antibody of the invention.

The amount of diagnostic antibody used in the various tests should be sufficient to achieve the diagnostic discrimination appropriate to the test. The amount of antibody or antigen used in a diagnostic test is generally from 0.01 to 1 ug, preferably 0.1 to 1ug.

The test kits of this invention can be used to identify humans at risk of any human infection the infective agent of which is immunogenic to rabbits. Such kits will contain an antibody of the invention which may be labelled or unlabelled depending on the test, in an amount which is sufficient to produce a detectable product. The composition may additionally contain standard adjuvants such as buffers, stabilizers or isotonic solutions as well as reactants such as a second antibody.

Embodiments of the invention are described hereinafter by way of examples only. In the examples which follow, reference will be made to media by name, the name corresponding to the media compositions set out below:

1. Growth Medium: Dubelcco's modified Eagle's medium (DMEM) a product of Gibco, supplemented with 4.5 g/l glucose, 33.3 mM sodium bicarbonate, 20 mM HEPES, 2 mM L-glutamine, 1 mM sodium pyruvate, 50 I.U./mL penicillin, and 50 ug/ml streptomycin.
2. RMH Culture Medium: Growth medium (1) supplemented with heat inactivated normal rabbit serum at 15% v/v unless otherwise stated.
3. RMH Selection and Culture Medium: RMH culture medium (2) supplemented with HAT medium.

EXAMPLE 1

Normal Rabbit Serum Production

Normal rabbit serum (NRS) used was a pool of sera collected from non-immunized rabbits whose serum supported the growth of Sp 2/0 cells at 10% in DMEM and did not show anti-Group A Streptococcus activity determined by ELISA. Blood was collected from the rabbit ear vein into glass tubes and left overnight at 4° C. The blood cells and clots were removed by centrifugation at 400 xg for 20 minutes. The supernatants (= serum) were collected, heat inactivated (56° C./30min) and then filter sterilized. The filtrates were kept at −80° C. in 50 ml aliquots until use.

EXAMPLE 2

Extraction of Rabbit Immunocytes

The hyperimmunized rabbit was sacrificed by stunning the head. The organs such as lymph nodes and spleen were surgically removed using a sterile technique. The organs were immediately placed in a wide necked bottle with a cap containing warm medium with antibiotics and 20% serum (e.g. heat inactivated FCS) (=transport medium), and were brought to laminar flow hood. The organs were then immediately processed for immunocyte isolation. To isolate iummunocytes specifically from spleen, the spleen was placed in a 100 mm petri dish containing 10 ml warm transport medium. Any extra tissue attached to the organ was removed. A portion of the spleen was cut and transferred to another petri dish with medium which was then cut into approximately 5 mm$^2$ size with sterile scissors. The pieces of spleen were pressed against the stainless steel screen (50 mesh size, 43 cm diameter) with a glass syringe plunger in circular movements until only fibrous tissue remained. The serum was rinsed with warm transport medium. The spleen cell suspension was transferred to 15 ml centrifuge tubes. Using a 10 ml pipette, the clumps were dispersed. The suspension was stood for 3 minutes at RT and the top 95% of the cell suspension was transferred to another centrifuge tube, and viable cell count performed and a desired number selected.

EXAMPLE 3

Conditioning of Murine Myelomas

Myelomas are normally maintained in a growth medium (e.g., DME, RPMl-1640) supplemented with 10% FCS. Adaptation to normal rabbit serum (NRS) is carried out by gradually increasing the ratio of NRS to FCS (5% FCS/5% NRS for 48 hours followed by 2.5% FCS/7.5% NRS for 48 hours, then completely switching to NRS (10%) and continue culture for additional 6 days prior to harvesting for cell fusion).

EXAMPLE 4

Fusion

Approximately $2\times10^8$ rabbit immunocytes extracted as described in example 2 were mixed with $4\times10^7$ cells of the murine myeloma line Sp2/0-Ag14 (ATCC CRL 1581) conditioned as in Example 3 and previously washed in growth medium (1). Immunocytes and myelomas were copelleted. The pellet was warmed for 2 minutes in a water bath at 37° C. and then exposed to PEG 4000 (final concentration in tube =43% w/v) for one minute. The mixture was centrifuged at 100mg for two minutes, and then supplemented with additional aliquots of growth medium ultimately to fill the tube and then centrifuged at room temperature.

The supernatant was aspirated, and the cell pellet resuspended in RMH selection and culture medium (3) and incubated at 37° C. in $CO_2$ atmosphere for 30 minutes. Aliquots of 100 μl from the cell suspension were delivered into wells and then incubated at 37° C./8% $CO_2$/98% relative humidity with periodic supplementation of each well with additional RMH selection and culture medium.

Supernatant from wells exhibiting growth was screened for antibody using the ELISA technique. PVC microtiter plates coated with an optimized dilution (in 0.1M carbonate/bicarbonate buffer, pH 9.6) of nitrous acid extract from Streptococcus cells of groups A, B, C, D, F or G (ATCC nos. 19615, E13813, 12388, 19433, 12392 or 12394 recommended by ATCC as being Type strains antigenically representative of these groups, respectively). Positive cultures were detected with an optimized dilution of urease-conjugated sheep anti-rabbit IgG (H an L chain specific) and urease substrate, and confirmed to be secreting rabbit immunoglubulin using this conjugate and optimally diluted urease conjugated rabbit anti-mouse F(ab)$_2$. The specificity of the former conjugate for rabbit immunoglubulin in the ELISA was established using titrations of Group A Streptococcus (GAS)-reactive rabbit and mouse antisera.

Cells produced by fusion of rabbit spleen immunocytes and murine Sp2/0-Ag14 myeloma cells, i.e., those cells contained in wells testing positive for Group A antibody, were resuspended in growth medium (1) supplemented either with 15% fetal calf serum (FCS) (Fusion A in Table 1) or with 15% normal rabbit serum (NRS) (Fusion B in Table 1 below) and distributed into tissue culture plates with feeder cells as detailed in Table 1. Initial examination of plates (four days post-fusion) indicated that hybridomas were growing in cultures supplemented with FCS far more rapidly than in cultures supplemented with NRS. Wells were refed with appropriately supplemented medium after 7 and 12 days post fusion. Seventeen days after fusion, culture supernatants from wells with actively growing hybridoma clones were screened for the presence of rabbit antibody against Group A Streptococcus (GAS) by ELISA. The data in Table 1 shows that, in spite of our initial observation, cultures supplemented with NRS produced more positive wells than those supplemented with FCS. Furthermore, cultures containing a feeder layer of peritoneal exudate cells (PECs) yielded considerably more positive wells than those containing splenocytes/thymocytes. These observations strongly suggest that the presence of rabbit serum and peritoneal exudate cells in hybridoma cultures increased the number of clones secreting GAS reactive rabbit antibody

TABLE 1

The Effect of Serum and Feeder Cell Type on Outcome of Fusion Between Hyperimmune Rabbit Spleen Cells and Murine SP2/0 Plasmacytoma Cells

| Cell Fusion | Serum Supplement | Feeder Cells | Appearances of Cultures on Day 4 Post-Fusion | Number of Wells Positive in Initial ELISA[3] | Cell Growth on Day 17 Post-Fusion |
|---|---|---|---|---|---|
| A | 15% FCS | Spl./thy[1] | Multiple RMH in every well, most at 16 cell-stage | 13% (40/300) | Massive fibroblastic cell growth, outgrowing hybridomas |
|  |  | PEC[2] |  | 30% (18/60) | Few areas of fibroblastic cell growth. Good hybridoma growth. |
| B | 15% NRS | Spl./thy[1] | Many viable cells in every well, but no cell division | 55% (159/288) | Minimal fibroblastic cell growth. Good hybridoma growth easily observed. |
|  |  | PEC[2] |  | 90% (54/60) |  |

[1] spl/thy: splenocytes/thymocytes
[2] PEC: Peritoneal exudate cells
[3] Initial ELISA screening for GAS reactive wells was performed on Day 17 post fusion In view of the extremely high total number of ELISA positive wells (271), a smaller number of primary hybridomas was selected for cloning. Selection of those giving the higher OD$_{590}$ in the GAS-ELISA reduced the number to 111 (approximately equal numbers from each fusion for subsequent comparison to RMH stability) and selection of the most rapid growers reduced it still more to 44 (Table 2). It is noteworthy that during passage prior to cloning, considerably more primary hybridomas from fusion A (growth medium supplemented with FCS) were discarded because of loss of antibody production or poor growth rates, than from fusion B (growth medium supplemented with NRS) (Table 2). Of 44 primary RMH's cloned by limiting dilution, 41 cloned and stabilized successfully. None of the clones from fusion A (in calf serum) survived cloning, but 95% of those from fusion B (in rabbit serum) cloned and continued to secrete rabbit antibody. Of these 41 RMH cell lines, 28 (68%) cloned and stabilized successfully after one cloning cycle, 11 (95%) stabilized after 2 cloning cycles, and the remaining 2 (hybridoma lines stabilized (100%) after three cycles, ELISAs conducted on supernatants of each hybridoma line, using PVC plates coated with nitrous acid extracts of groups A, B, C, D, F and G Streptococci, confirmed that all 41 lines secreted GAS-specific rabbit MAbs. ELISAs where peroxidase conjugates specific for rabbit IgG ($\gamma$ chain) and IgM ($\mu$ chain) and recrystallized 5-aminosalicyclic acid chromogen and substrate were substituted for the UREIASE ™ (ALLELIX, INC.) reagents, showed that 39 RMH lines secreted rabbit IgG, whilst the other two secreted rabbit IgM.

TABLE 2

History of Rabbit Mouse Monoclonal Hybridomas Producing A Streptococcus Specific Rabbit Monoclonal Antibody

| Number of Primary Hybridomas That: | Fusion Reference A | B |
|---|---|---|
| Were positive in GAS-ELISA screen in initial 96 well plates | 58/360 (16%) | 213/348 (61%) |
|  | ↓ Selected wells giving highest OD$_{590}$ in Group A Streptococcus ELISA | ↓ |
| Were passaged to 24 well plate | 48/58 (83%) | 63/213 (30%) |
|  | ↓ Selected most rapid growers | ↓ |
| Were cloned by limiting dilution | 1/48 (0%) | 41/63 (68%) |

TABLE 2-continued

History of Rabbit Mouse Monoclonal Hybridomas Producing A Streptococcus Specific Rabbit Monoclonal Antibody

| Number of Primary Hybridomas That: | Fusion Reference A | B |
|---|---|---|
| Were successfully cloned | 0/1 (0%) | 41/43 (95%) |
| Produced monoclonal RMH lines that secrete Group A Streptococcus specific monoclonal antibody | 0/0 (0%) | 41/41 (100%) |
| Produced monoclonal RMH lines that secrete rabbit IgG | 0/0 (0%) | 39/41 (95%) |

The data in Table 2 suggest that RMHs cultured in the presence of NRS i.e., in RMH culture medium, were far more stable in terms of rabbit antibody secretion, than those cultured in the presence of FCS. To test this hypothesis, a further ten primary hybridomas were cloned in duplicate, one replicate in DMEM supplemented with 7.5% FCS and 7.5% NRS the other with 15% FCS. The data in Table 3 shows that although nine out of these ten primary hybridomas cloned successfully in medium containing FCS alone and continued to form rapidly growing colonies, stabilization of rabbit antibody production was considerably more efficient in those cloned in the presence of NRS.

TABLE 3

Importance of NRS as Medium Supplement for Establishment of Specific-antibody Secreting RMHs

| RMH Line | Serum | Number of ELISA Positive Wells Number of Wells Screened | Percent Positive |
|---|---|---|---|
| B 102 | 7.5% FCS/7.5% NRS | 26/26 | 100 |
|  | 15% FCS | 5/21 | 24 |
| B 104 | FCS/NRS | 31/31 | 100 |
|  | FCS | 0/21 | 0 |
| B 107 | FCS/NRS | 19/23 | 83 |
|  | FCS | 0/36 | 0 |
| B 120 | FCS/NRS | 25/26 | 96 |
|  | FCS | 0/23 | 0 |
| B 130 | FCS/NRS | 12/14 | 86 |
|  | FCS | 0/34 | 0 |
| B 139 | FCS/NRS | 33/37 | 89 |
|  | FCS | 4/28 | 14 |
| B 157 | FCS/NRS | 17/25 | 68 |
|  | FCS | 10/28 | 36 |
| B 158 | FCS/NRS | 31/31 | 100 |
|  | FCS | 5/17 | 0 |
| B 172 | FCS/NRS | 26/26 | 100 |
|  | FCS | 7/21 | 33 |
| B 174 | FCS/NRS | 10/10 | 100 |

TABLE 3-continued

Importance of NRS as Medium Supplement for Establishment of Specific-antibody Secreting RMHs

| RMH Line | Serum | Number of ELISA Positive Wells Number of Wells Screened | Percent Positive |
|---|---|---|---|
| | FCS | 0/0 | 0 |

Ten primary RMH Lines were cloned in duplicate, one replicate of each in DMEM supplemented with 7.5% FCS and 7.5% NRS, the other with 15% FCS. Plates were examined for clonal growth after 8-10 days, and supernatants from wells containing growing clones wee screened for GAS specific rabbit antibody by ELISA.

The efficiency of MAb production in vitro was studied using eight RMH lines. These lines have continued to secrete GAS-specific rabbit MAb during 4 months of continuous in vitro culture, and through at least two cycles of freezing in liquid nitrogen followed by thawing and culture. Each line was adapted, after stabilization, to grow in DMEM containing 10% FCS. Rabbit MAb was affinity-purified from culture supernatants using a Sepharose-anti-rabbit IgA immunoadsorbent column. The yields and specificities of the antibody purified from the eight RMH line supernatants are shown in Table 4. The yields of MAb obtained were in a similar range to what might be expected for murine MAb from murine hybridomas when cultured in vitro. However, all eight RMH lines produced rabbit (and not mouse) antibody that exhibited specific reactivity with nitrous acid extract from Group A Streptococcus, but not from antigenic type strains of B, C, D, F or G Streptococci.

TABLE 4

Yields and Specificities of Affinity Purified Rabbit MAbs from Eight RMH Line after Adaptation to Grow in DMEM Containing FCS Rather than NRS

| RMH Line | B52 | B62 | B85 | B100 | B111 | B205 | B241 | B246 |
|---|---|---|---|---|---|---|---|---|
| Yield[1] (μg/ml) | 8.76 | 7.28 | 5.62 | 5.40 | 5.42 | 3.96 | 3.04 | 3.26 |
| OD$_{590}$ matrix in ELISA[2] for detecting Streptococcus specific: Rabbit antibody against Group A | 5 | 2 | 1 | 1 | 1 | 1 | 1 | 1 |
| Rabbit antibody against Group B, C, D, F and G | 0 | 0 | 0 | 0 | 0 | 0 | 0 | 0 |
| Mouse antibody against Group A | 0 | 0 | 0 | 0 | 0 | 0 | 0 | 0 |
| Mouse antibody against Group B C, D, F and G | 0 | 0 | 0 | 0 | 0 | 0 | 0 | 0 |

[1]Yield of protein (OD$_{280}$) affinity purified form RMH culture supernatant containing 10% FCS, after subtracting yield of protein affinity purified from DMEM containing 10% FCS.
[2]Eluates from anti-rabbit IgG immunoadsorbent were tested undiluted by indirect ELISA on PVC microtitre plates coated with optimally diluted nitrous acid extracts of streptococcal groups A, B, C, D, F and G, using rabbit and mouse immunoglobulin specific conjugates. OD$_{590}$ matrix readings were taken 30 minutes after substrate addition to wells.

Karyotyping of one RMH was performed to ascertain the number of chromosomes present at various times after fusion. Table 5 shows that 64 days post fusion the mean chromosome number of this line has stabilized to approximately the same as the parent SP2/0 cells, with a coefficient of variation less than half of that of the SP2/0s. The karyotypes of four other RMH lines were also examined three months post fusion, and found to contain a similar number of chromosomes. All these RMH lines appeared to contain 2-3 rabbit chromosomes, in addition to their complement of mouse chromosomes.

TABLE 5

Chromosome Numbers of Normal Rabbit Lymphocytes, Murine SP2/0-Ag 14 Cells and RMH Cells at Various Time Post Fusion

| | Murine SP2/0-Ag 14 | Rabbit Lymphocytes | RMH-B52 | | |
|---|---|---|---|---|---|
| | | | Day 32 | Day 36 | Day 64 |
| Number of Spreads Counted | 45 | 50 | 28 | 38 | 34 |
| X (2N chromosomes) numbers) | 65 | 43.9 | 82 | 73.5 | 69.2 |
| SD | 8.5 | 1.0 | 14.2 | 5.4 | 3.9 |
| CV | 13.3% | 2% | 17.3% | 7.3 | 5.6% |

X = mean number of chromasomes per cell
SD = standard deviation
CV = coefficient of variation Thus, while rabbit-mouse hybridomas have been produced using procedures conventional in the art, these hybridomas have shown extreme instability and a general inability to secrete a complete rabbit antibody having the intended specificity. We have developed optimized procedures for production of large numbers of stable RMHs, that secrete intact rabbit immunoglobulin molecules, with excellent specificity to the immunogen employed. These procedures include the use of the SP2/0-Ag14 myeloma line as fusion partner, culture of RMHs after fusion in the presence of NRS and PEC feeder cells, cloning of RMHs in medium containing NRS, and once stabilized, gradual adaptation of monoclonal RMH lines to grown in medium containing FCS rather than NRS. This final procedure facilitates affinity purification of the rabbit MAb from culture supernatants free of contaminating rabbit antibody from NRS.

Production of suitable MAbs against certain epitopes and immunogens has been prevented by poor immune responses of mice, or even rats, against them. The immunogenicity of these molecules can however, vary considerably between different species, and rabbits, as a species, are sufficiently distant from mice that their immune systems usually respond well to epitopes against which mice are poor responders. The ability to use spleen cells from specifically hyperimmunized rabbits for generation of large numbers of stable RMH lines that secrete rabbit monoclonal antibody against these immunogens allows production of new monoclonal antibody species that, to date, could not be produced.

What is claimed is:

1. A stable rabbit-mouse hybridoma which secretes intact rabbit monoclonal antibody of defined specificity produced by the process of culturing the hybridoma in a nutrient medium containing rabbit serum.

2. A hybridoma of claim 1 identified as ATCC HB 9696.

3. A method for increasing the efficiency of producing stable rabbit-mouse hybridomas which secrete intact rabbit monoclonal antibody of defined specificity which comprises culturing the hybridoma in a nutrient medium containing rabbit serum.

4. The hybridoma defined in claim 1 which secretes rabbit monoclonal antibody specific for Group A Streptococcus.

5. The method according to claim 3 wherein the rabbit serum is heat inactivated normal rabbit serum.

6. The method according to claim 5 wherein said normal rabbit serum is present in the nutrient medium in which the hybridomas is cultured in an amount from 5 to 25%.

7. The method according to claim 6 wherein the normal rabbit serum is present in an amount from 10 to 20% v/v.

8. The method according to claim 3 wherein the hybridoma is cultured initially in the presence of peritoneum exudate cells.

9. A method for increasing the efficiency of producing rabbit-mouse hybridomas which secrete intact antibodies specific for an immunogen which comprises fusing an immunocyte extracted from a rabbit hyperimmunized with the said immunogen, with a murine myeloma cell which is incapable of producing murine immunoglobulin to form a hybridoma thereof;
  culturing the hybridoma in a nutrient medium supplemented with normal rabbit serum and, initially, in the presence of feeder cells and, later, in the absence of said feeder cells, and
  cloning those hybridomas which secrete said antibody through at least two cloning cycles
  the efficiency of production of the hybridoma being increased due to the presence of rabbit serum in the nutrient medium.

10. The method according to claim 9 wherein the murine myeloma cell has been pre-conditioned to grow in the presence of normal rabbit serum before being fused with the immunocyte.

11. The method according to claim 9 wherein the murine myeloma cell has the desirable characteristics of the cell line Sp2/O-Ag14 (ATCC CRL 1581).

12. The method according to claim 11 wherein the feeder cells are murine peritoneum exudate cells.

13. A method as in claim 3, 5, 6, 7 or 8 including the step of recovering the rabbit monoclonal antibody.

14. The method according to claim 13 which comprises the additional, later step of growing the stable hybridoma in the presence of nutrient lacking normal rabbit serum prior to recovering rabbit monoclonal antibody.

15. A composition containing a diagnostically effective amount of a rabbit monocular antibody wherein the antibody is derived from the hybridoma identified as ATCC HB 9696.

16. A diagnostic kit for detecting a human at risk of a disease, the effective agent of which is an antigen which will stimulate an immune response in a rabbit, said kit comprising a container which contains a sufficient amount of a rabbit monoclonal antibody derived from a stable rabbit-mouse hybridoma of claim 1 to react specificity with said antigen and produce a detectable product.

17. A diagnostic kit of claim 16 the antibody is specific for Group A Streptococcus.

18. A diagnostic kit of claim 16 wherein the antibody is derived from the hybridoma identified as ATCC HB 9696.

* * * * *